US00PP30694P3

(12) United States Plant Patent
O'Connell

(10) Patent No.: US PP30,694 P3
(45) Date of Patent: Jul. 9, 2019

(54) *KALANCHOE* PLANT NAMED 'DRAGONFIRE'

(50) Latin Name: *Kalanchoe hybrid*
Varietal Denomination: Dragonfire

(71) Applicant: Altman Specialty Plants, Inc, Vista, CA (US)

(72) Inventor: Renee O'Connell, Escondido, CA (US)

(73) Assignee: Altman Specialty Plants Inc., Vista, CA (US)

( * ) Notice: Subject to any disclaimer, the term of this patent is extended or adjusted under 35 U.S.C. 154(b) by 0 days.

(21) Appl. No.: 15/732,289

(22) Filed: Oct. 18, 2017

(65) Prior Publication Data

US 2019/0116705 P1 Apr. 18, 2019

(51) Int. Cl.
*A01H 5/02* (2018.01)

(52) U.S. Cl.
USPC ..... Plt./335

(58) Field of Classification Search
USPC ..... Plt./335
See application file for complete search history.

*Primary Examiner* — Keith O. Robinson
(74) *Attorney, Agent, or Firm* — Cassandra Bright

(57) ABSTRACT

A new and distinct *Kalanchoe* cultivar named 'Dragonfire' is disclosed, with plants comprised of apple green leaves with red margins. In bright light or during cooler climates, the leaves blush intensely, becoming largely red with green only near the center of the plant. The new cultivar 'Dragonfire' exhibits robust and rapid growth, enhancing finished pot production times. The new cultivar has proven landscape and full sun tolerant, including at elevations around 1400 feet in Southern California. The new variety is an *Kalanchoe*, part of the Crassulaceae complex that includes *Aeonium, Echeveria, Graptopetalum, Sedum* and others. *Kalanchoe* is a popular genus, typically produced for the floriculture industry, as well as for uses as container plants for the patio, or as landscape plants.

1 Drawing Sheet

Latin name of the genus and species: *Kalanchoe* hybrid. Variety denomination: 'DRAGONFIRE'.

BACKGROUND OF THE INVENTION

The new cultivar is a product of a planned breeding program. The new variety originated from a cross pollination of an unnamed, unpatented proprietary seed parent of *Kalanchoe luciae* with the pollen parent of an unpatented, proprietary *Kalanchoe hybrida* referred to as *Kalanchoe* '21'. The cross pollination was made during December 2015 in Vista, Calif., at a commercial greenhouse. The new cultivar 'Dragonfire' was discovered by the inventor, Renee O'Connell in July 2016 in Vista, Calif., at a commercial greenhouse.

Asexual reproduction of the new cultivar 'Dragonfire' was first performed in Vista, Calif., at a commercial greenhouse, by terminal vegetative cuttings in July 2016. *Kalanchoe* 'Dragonfire' has since produced multiple generations and has shown that the unique features of this cultivar are stable and reproduced true to type.

SUMMARY OF THE INVENTION

The cultivar 'Dragonfire' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DRAGONFIRE'. These characteristics in combination distinguish 'DRAGONFIRE' as a new and distinct *Kalanchoe* cultivar:

1. The new cultivar *Kalanchoe* 'Dragon Fire' forms plants comprised of apple green leaves with red margins. In bright light or during cooler climates, the leaves blush intensely, becoming largely red with green only near the center of the plant.
2. *Kalanchoe* 'Dragon Fire' offsets at an early size; at approximately 4-6" tall, creating an attractive cluster of apple green, accentuated by red.
3. The diameter of the new cultivar *Kalanchoe* 'Dragon Fire' can exceed 6" in diameter while offsets are still small; as a result, a single cutting fills a 1 gallon pot readily.
4. *Kalanchoe* 'Dragon Fire' has been proven landscape tolerant at 1400' elevation in Escondido, Calif.
5. *Kalanchoe* 'Dragon Fire' is fast-growing, enhancing production times in a commercial nursery.

PARENTAL COMPARISON

Plants of the new cultivar are similar to plants of the seed parent, in most horticultural characteristics, however, plants of the new cultivar differ in the following:

1. *Kalanchoe* 'Dragon Fire' offsets readily at an early age, whereas the seed parent does not offset until it becomes older, and then offsets sporadically, typically at the onset of flowering.
2. *Kalanchoe* 'Dragon Fire' exhibits an attractive contrast between the apple green color and the accentuating red blush, whereas the seed parent displays a pruinose mint green color, typical of *Kalanchoe luciae*, accentuated with a pruinose red, resulting in a less attractive contrast between the two colors.

3. *Kalanchoe* 'Dragon Fire' grows faster than the seed parent, thereby enhancing production times in a commercial nursery.
4. *Kalanchoe* 'Dragon Fire', readily offsetting, forming attractive clusters in the landscape, whereas the seed parent, offsets sporadically, taking much longer to form clusters that are often very uneven, due to the sporadic nature of the offsetting.

Plants of the new cultivar are similar to plants of the pollen parent, in most horticultural characteristics, however, plants of the new cultivar differ in the following;

1. *Kalanchoe* 'Dragon Fire' forms attractive, semi-rosette plants, whereas *Kalanchoe* '21' tends to be a taller, lankier growing plant.
2. *Kalanchoe* 'Dragon Fire', exhibits an attractive contrast between the apple green leaves and the red blush, whereas *Kalanchoe* '21' is a darker green, resulting in a subdued contrast between the dark green and the red blush.
3. *Kalanchoe* 'Dragon Fire' forms semi-rosette plants that can fill a 1 gallon or 8" pot with 1 cutting, whereas it is necessary to plant multiple cuttings of *Kalanchoe* '21' or pinch several times to fill the same sized pot, thereby enhancing production in a commercial nursery.
4. The leaves of *Kalanchoe* 'Dragon Fire' have smooth margins, with a few rare crenations, whereas the leaves of *Kalanchoe* hybrid '21' are irregularly dentate, to variably crenate.

COMMERCIAL COMPARISON

The new cultivar 'Dragon Fire' can be compared to the unpatented commercial *Kalanchoe orgyalis*. Plants of the *Kalanchoe orgyalis* are similar to plants of the new cultivar 'Dragon Fire' in most horticultural characteristics. However, the new cultivar 'Dragon Fire' differs in the following:

1. *Kalanchoe* 'Dragon Fire' forms semi-rosette plants, becoming attractive clusters due to the free offsetting, as compared with *Kalanchoe orgyalis*, which grows as a shrub, 1-2 meters in height.
2. *Kalanchoe* 'Dragon Fire' produces an attractive contrast of apple-green leaves, with the apices, and often more of the leaf blushed red, particularly in bright light or cooler temperatures, whereas *Kalanchoe orgyalis* produces leaves that are pilose, and gray-bronze to ruddy copper in color.
3. Due to the earlier offsetting of *Kalanchoe* 'Dragon Fire', as compared with *Kalanchoe orgyalis*, the plant can be propagated more rapidly, enhancing production times in a commercial nursery.
4. *Kalanchoe* 'Dragon Fire' grows faster than does *Kalanchoe orgyalis*, allowing for faster production times in the commercial nursery.

The new cultivar 'Dragon Fire' can be compared to the unpatented commercial *Kalanchoe blossfeldiana*. Plants of *Kalanchoe blossfeldiana* are similar to plants of the new cultivar 'Dragon Fire' in most horticultural characteristics. However, plants of the new cultivar 'Dragon Fire' differ in the following:

1. *Kalanchoe* 'Dragon Fire' has proven landscape tolerant in full sun at 1400' elevation in Escondido, Calif., whereas *Kalanchoe blossfeldiana* is a plant better grown in a filtered light or shade.
2. *Kalanchoe* 'Dragon Fire' produces a semi-rosette plant, whereas *Kalanchoe blossfeldiana* is an upright subshrub.
3. *Kalanchoe* 'Dragon Fire' forms plants with apple-green leaves, contrasted attractively with red blushed leaf margins, whereas *Kalanchoe blosssfeldiana* produces plants with shiny, dark green leaves. In bright light or cooler temperatures, much of the leaf of *Kalanchoe* 'Dragon Fire' becomes red.
4. *Kalanchoe* 'Dragon Fire' can be sold as an attractive, colorful landscape accent or as a patio accent, whereas *Kalanchoe blossfeldiana* is typically sold as a houseplant.

BRIEF DESCRIPTION OF THE PHOTOGRAPH

The accompanying photograph illustrates in full color a typical plant of 'DRAGONFIRE', at about 6 months of age, grown in a greenhouse in Vista, Calif. The photograph was taken using conventional techniques and equipment. While the colors in these photographs may display variances of color as compared to the living cultivar, due to LRV (light reflectance value), they are as accurate as possible using conventional photographic techniques. Colors in the photographs may appear to differ slightly from the color values cited in the botanical description, which accurately describe the colors of the new *Kalanchoe* plant. The photograph depicts a plant grown under natural light conditions of approximately 4500 foot-candles during early Summer. Temperatures ranged from about 5° C. to 29° C. night and day. No artificial light, photoperiodic treatments or chemical treatments were given to the plants.

In the following description, color references are made to The Royal Horticultural Society Colour Chart, 2007, except where general terms of ordinary dictionary significance are used. The following observations and measurements describe 'Dragonfire' plants in a commercial greenhouse in Vista, Calif. Temperatures ranged from 34° F. to 90° F. night and day. No artificial light, photoperiodic treatments or chemical treatments were given to the plants. Natural light conditions were approximately 2500-4000 foot candles of light. Measurements and numerical values represent averages of typical plant types.

Botanical classification: *Kalanchoe hybrida* 'DRAGONFIRE'.

Propagation:

*Type of propagation typically used.*—Terminal vegetative cuttings.

*Time to initiate roots.*—About 10 days at approximately 24° C.

*Root description.*—Fibrous. Tan to brown, not accurately described with R.H.S. chart.

Plant:

*Age of plant described.*—Approximately 4 months from a cutting.

*Container size of the plant described.*—30 cm.

*Growth habit.*—Upright branching sub-shrub.

*Height.*—Approximately 28 cm to top of highest leaf.

*Plant spread.*—Approximately 27 cm. Plant comprised of 5 stems.

*Growth rate.*—Moderately fast.

*Branching characteristics.*—Freely branching from an early age.

Foliage:

*Leaf.*—Arrangement: Opposite. Average length: Approximately 15 cm. Average width: 8 cm. Width at base: 1.8 cm. Shape of blade: Oblanceolate. Apex: Rounded obtuse. Base: Broad attenuate. Margin: Irregular very shallow crenations. Texture of top surface: Glabrous. Texture of bottom surface: Glabrous. Quantity of leaves per plant: Approximately 12 to 20 per stem, 4 to 6 stems per plant.

*Color*.—Young foliage, upper side, near apex: Near RHS 46A. Young foliage, upper side, center: Near Yellow-Green 144A, lightly flushed Red 46A along margin. Young foliage upper side, near base: Near Yellow-Green 144A. Young foliage, under side, near apex: Near RHS 46A. Young foliage, under side, center: Near Yellow-Green 144A, lightly flushed Red 46A along margin. Young foliage under side, near base: Near Yellow-Green 144A. Mature foliage, upper side, near apex: Near RHS 46A. Mature foliage, upper side, center: Near Yellow-Green 144A, flushed Red 46A. Mature foliage upper side, near base: Near Yellow-Green 144A. Mature foliage, under side, near apex: Near RHS 46A. Mature foliage, under side, center: Near Yellow-Green 144A, flushed Red 46A. Mature foliage under side, near base: Near Yellow-Green 144A. Variegation: Absent.

*Venation*.—There is no visual appearance of venation. Indistinguishable from leaf blade.

Flower: Not observed.

Reproductive organs: Not observed.

Other characteristics:

*Fruits and seeds*.—Not observed.

*Temperature tolerance*.—Tolerates temperatures from approximately 0° C. to at least 32° C.

*Disease/pest resistance*.—Neither resistance nor susceptibility to normal diseases and pests of *Kalanchoe* observed.

*Drought tolerance*.—Tolerates at least 3 weeks of high temperatures without supplemental water, showing no serious damage to plant.

What is claimed is:

1. A new and distinct cultivar of *Kalanchoe* plant named 'DRAGONFIRE' as herein illustrated and described.

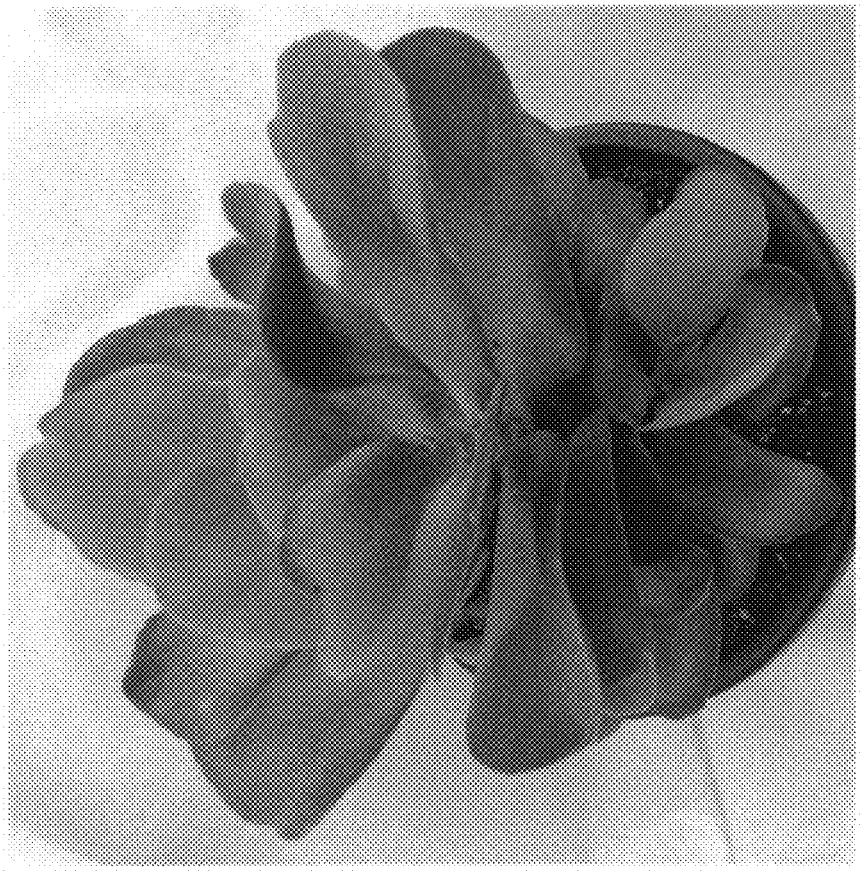

* * * * *